(12) United States Patent
Divino et al.

(10) Patent No.: US 10,433,853 B2
(45) Date of Patent: Oct. 8, 2019

(54) EMBOLIC MEDICAL DEVICES

(71) Applicant: Covidien LP, Mansfield, MA (US)

(72) Inventors: Vincent Divino, Mission Viejo, CA (US); Richard Rhee, Anaheim, CA (US); Earl Bardsley, San Clemente, CA (US); Julie Kulak, Trabuco Canyon, CA (US); Madhur Kadam, Lake Forest, CA (US); Ramon Carrillo, Santa Ana, CA (US); Kokou A. Amefia, Irvine, CA (US); Khoa Vu, Santa Ana, CA (US)

(73) Assignee: Covidien LP, Mansfield, MA (US)

( * ) Notice: Subject to any disclaimer, the term of this patent is extended or adjusted under 35 U.S.C. 154(b) by 236 days.

(21) Appl. No.: 15/630,887

(22) Filed: Jun. 22, 2017

(65) Prior Publication Data

US 2017/0281194 A1 Oct. 5, 2017

Related U.S. Application Data

(63) Continuation of application No. 14/256,032, filed on Apr. 18, 2014, now Pat. No. 9,713,475.

(51) Int. Cl.
*A61M 29/00* (2006.01)
*A61B 17/12* (2006.01)
*A61B 17/00* (2006.01)
*A61B 90/00* (2016.01)

(52) U.S. Cl.
CPC .. *A61B 17/12172* (2013.01); *A61B 17/12113* (2013.01); *A61B 17/12168* (2013.01); *A61B 17/12177* (2013.01); *A61B 2017/00867* (2013.01); *A61B 2017/1205* (2013.01); *A61B 2090/0801* (2016.02); *A61B 2090/3966* (2016.02)

(58) Field of Classification Search
CPC ........ A61B 17/12172; A61B 17/12177; A61B 17/12113; A61B 17/12168; A61B 2090/3966; A61B 2090/0801; A61B 2017/1205; A61B 2017/00867
See application file for complete search history.

(56) References Cited

U.S. PATENT DOCUMENTS 5,354,295 A 10/1994 Guglielmi et al.
5,669,931 A 9/1997 Kupiecki et al.
(Continued)

FOREIGN PATENT DOCUMENTS

JP 2003265620 A 9/2003
WO 2011066962 A1 6/2011
(Continued)

*Primary Examiner* — Amy R Weisberg
(74) *Attorney, Agent, or Firm* — Fortem IP LLP; Vijay Kumar

(57) ABSTRACT

An occlusive device for occluding a target area can include an elongate member having opposing first and second side edges extending longitudinally along the member and a member width. The member can have a collapsed configuration in which the first and second side edges are curled toward each other about a longitudinal axis of the member. Further the member can have an expanded configuration in which the member form a series of loops and the first and second side edges uncurl to be spaced apart from each other.

20 Claims, 14 Drawing Sheets

(56) References Cited

U.S. PATENT DOCUMENTS

| | | | |
|---|---|---|---|
| 5,676,697 A * | 10/1997 | McDonald | A61F 2/07 623/1.35 |
| 5,792,157 A | 8/1998 | Mische et al. | |
| 5,951,599 A | 9/1999 | McCrory | |
| 6,066,158 A | 5/2000 | Engelson et al. | |
| 6,254,628 B1 | 7/2001 | Wallace et al. | |
| 6,309,367 B1 | 10/2001 | Boock | |
| 6,602,261 B2 | 8/2003 | Greene et al. | |
| 6,605,101 B1 | 8/2003 | Schaefer et al. | |
| 6,878,384 B2 | 4/2005 | Cruise et al. | |
| 6,994,689 B1 | 2/2006 | Zadno-Azizi et al. | |
| 7,229,461 B2 | 6/2007 | Chin et al. | |
| 7,601,160 B2 | 10/2009 | Richter | |
| RE42,625 E | 8/2011 | Guglielmi | |
| 8,043,326 B2 | 10/2011 | Hancock et al. | |
| 8,425,541 B2 | 4/2013 | Masters et al. | |
| 8,470,013 B2 | 6/2013 | Duggal et al. | |
| 8,715,317 B1 | 5/2014 | Janardhan et al. | |
| 8,906,057 B2 | 12/2014 | Connor et al. | |
| 9,211,202 B2 | 12/2015 | Strother et al. | |
| 9,486,224 B2 | 11/2016 | Riina et al. | |
| 9,833,309 B2 | 12/2017 | Levi et al. | |
| 9,844,380 B2 | 12/2017 | Furey | |
| 9,907,684 B2 | 3/2018 | Connor et al. | |
| 9,962,146 B2 | 5/2018 | Hebert et al. | |
| 10,028,745 B2 | 7/2018 | Morsi | |
| 2001/0000797 A1 | 5/2001 | Mazzocchi | |
| 2001/0001835 A1 | 5/2001 | Greene et al. | |
| 2003/0018294 A1 | 1/2003 | Cox | |
| 2003/0028209 A1 | 2/2003 | Teoh et al. | |
| 2003/0040772 A1 | 2/2003 | Hyodoh et al. | |
| 2005/0267511 A1 | 12/2005 | Marks et al. | |
| 2005/0277978 A1 | 12/2005 | Greenhalgh | |
| 2006/0116713 A1 | 6/2006 | Sepetka et al. | |
| 2006/0155323 A1 | 7/2006 | Porter et al. | |
| 2006/0200234 A1 | 9/2006 | Hines | |
| 2006/0206199 A1 | 9/2006 | Churchwell et al. | |
| 2006/0253148 A1 | 11/2006 | Leone et al. | |
| 2007/0100426 A1 | 5/2007 | Rudakov et al. | |
| 2007/0175536 A1 | 8/2007 | Monetti et al. | |
| 2007/0191924 A1 | 8/2007 | Rudakov | |
| 2007/0265656 A1 | 11/2007 | Amplatz et al. | |
| 2008/0097401 A1 | 4/2008 | Trapp et al. | |
| 2008/0097508 A1 * | 4/2008 | Jones | A61B 17/12022 606/191 |
| 2009/0025820 A1 | 1/2009 | Adams | |
| 2009/0326639 A1 * | 12/2009 | Edin | A61F 2/06 623/1.15 |
| 2010/0144895 A1 | 6/2010 | Porter | |
| 2011/0082493 A1 | 4/2011 | Samson et al. | |
| 2011/0137405 A1 | 6/2011 | Wilson et al. | |
| 2011/0213405 A1 | 9/2011 | Porter et al. | |
| 2012/0239074 A1 | 9/2012 | Aboytes et al. | |
| 2012/0316632 A1 | 12/2012 | Gao | |
| 2013/0066357 A1 | 3/2013 | Aboytes et al. | |
| 2013/0116722 A1 | 5/2013 | Aboytes et al. | |
| 2013/0274866 A1 | 10/2013 | Cox et al. | |
| 2014/0012307 A1 | 1/2014 | Franano et al. | |
| 2014/0058420 A1 | 2/2014 | Hannes et al. | |
| 2014/0243881 A1 * | 8/2014 | Lees | A61F 2/013 606/200 |
| 2014/0316012 A1 | 10/2014 | Freyman et al. | |
| 2014/0371734 A1 | 12/2014 | Truckai | |
| 2015/0216684 A1 | 8/2015 | Enzmann et al. | |
| 2015/0250628 A1 | 9/2015 | Monstadt et al. | |
| 2015/0313737 A1 | 11/2015 | Tippett et al. | |
| 2015/0327843 A1 | 11/2015 | Garrison | |
| 2016/0066921 A1 | 3/2016 | Seifert et al. | |
| 2016/0135984 A1 | 5/2016 | Rudakov et al. | |
| 2016/0206320 A1 | 7/2016 | Connor | |
| 2016/0206321 A1 | 7/2016 | Connor | |
| 2017/0150971 A1 | 6/2017 | Hines | |
| 2017/0156903 A1 | 6/2017 | Shobayashi | |
| 2017/0189035 A1 | 7/2017 | Porter | |
| 2017/0266023 A1 | 9/2017 | Thomas | |
| 2017/0340333 A1 | 11/2017 | Badruddin et al. | |
| 2017/0367708 A1 | 12/2017 | Mayer et al. | |
| 2018/0049859 A1 | 2/2018 | Stoppenhagen et al. | |
| 2018/0125686 A1 | 5/2018 | Lu | |
| 2018/0140305 A1 | 5/2018 | Connor | |
| 2018/0161185 A1 | 6/2018 | Kresslein et al. | |
| 2018/0193025 A1 | 7/2018 | Walzman | |
| 2018/0193026 A1 | 7/2018 | Yang et al. | |
| 2018/0206852 A1 | 7/2018 | Moeller | |
| 2018/0263238 A1 * | 9/2018 | Flanagan | A61F 2/022 |
| 2019/0053811 A1 | 2/2019 | Garza et al. | |

FOREIGN PATENT DOCUMENTS

| | | |
|---|---|---|
| WO | 2011106426 A1 | 9/2011 |
| WO | 2017074411 A1 | 5/2017 |
| WO | 2018051187 A1 | 3/2018 |

* cited by examiner

EMBOLIC MEDICAL DEVICES

CROSS-REFERENCE TO RELATED APPLICATION

The present application is a continuation of U.S. patent application Ser. No. 14/256,032, filed Apr. 18, 2014, the disclosure of which is incorporated herein by reference in its entirety.

BACKGROUND

Field of the Inventions

The present disclosures relate to implantable devices. More specifically, the present disclosures relate to occlusive devices that can be implanted endovascularly, and in some embodiments, for aneurysm therapy.

Description of the Related Art

Numerous embolization devices have been provided for aneurysm treatment. Generally, braid-ball embolic devices, coils, and other types of embolization operate through blood flow disruption and subsequent thrombus formation. Currently, aneurysms are treated with embolic coils, such as Covidien Axium™ or Stryker GDC®10. These embolic devices are small coils with outside diameters ranging from 0.0090 inches to 0.0145 inches. The devices are heat treated on mandrels to impart a two or three-dimensional shape that are favorable for aneurysm geometries.

SUMMARY

At least one aspect of the disclosure provides methods and apparatuses for delivering an occluding device or devices (e.g., stent or stents) in the body. The occluding device can easily conform to the shape of the tortuous vessels of the vasculature. The occluding device can be used in a variety of applications. For example, in some embodiments, the occluding device can direct the blood flow within a vessel away from an aneurysm by substantially or fully blocking a neck of the aneurysm or substantially or fully disrupting blood flow within an aneurysm. Further, embodiments of the occluding devices disclosed herein provide numerous advantages in a single device that were only available previously by using a combination of different medical devices.

In accordance with some embodiments, a device is disclosed that can have a flattened profile and formed from either a tubular material or a flat sheet. The device can be heat treated to impart a two or three-dimensional shape.

The device can be made from polymers, metals or a combination of polymers and metals. The device can be braided, knitted or woven with multiple filaments within a single stitch or carrier. Radiopaque filaments can be added to enhance visibility during and after delivery to target vasculature. Embodiments of the device can have a wider profile than a coil and therefore, compared to coils, require fewer devices to obtain adequate aneurysm neck coverage and aneurysm sac stasis. The device can also provide superior framing support of the aneurysm sac.

In accordance with some embodiments, a method of delivering one or more devices comprises forming the device into a cylindrical or "spiral" shape and delivering it through a catheter. Forming the device into a cylindrical or spiral shape can minimize the crossing profile and allow access to distal anatomy. Thus, some embodiments can be used in vasculature that is smaller than that possible for traditional stents or other such expandable structures. Further, the pushing resistance of the device can be decreased, thereby improving the pushability of the device.

The subject technology is illustrated, for example, according to various aspects described below. Various examples of aspects of the subject technology are described as numbered clauses or embodiments (1, 2, 3, etc.) for convenience. These are provided as examples and do not limit the subject technology. It is noted that any of the dependent clauses may be combined in any combination with each other or one or more other independent clauses, to form an independent clause. The other clauses can be presented in a similar manner. The following is a non-limiting summary of some embodiments presented herein:

Clause 1. An occlusive device for occluding a target area, comprising: an elongate member having opposing first and second side edges extending longitudinally along the member and a member width, the member having (i) a collapsed configuration in which the first and second side edges are curled toward each other about a longitudinal axis of the member, and (ii) an expanded configuration in which the member form a series of loops and the first and second side edges uncurl to be spaced apart from each other.

Clause 2. The device of Clause 1, wherein the first and second side edges uncurl to be spaced apart from each other at no more than twice the member width.

Clause 3. The device of Clause 2, wherein the first and second side edges uncurl to be spaced apart from each other at approximately the member width.

Clause 4. The device of any one of the preceding clauses, wherein the elongate member comprises a shape memory material.

Clause 5. The device of Clause 4, wherein the elongate member comprises a material that is in austenite state when in the expanded configuration.

Clause 6. The device of any one of the preceding clauses, wherein the elongate member comprises a flattened tubular member.

Clause 7. The device of any one of the preceding clauses, wherein the member comprises a plurality of filaments.

Clause 8. The device of Clause 7, wherein a spacing of the filaments varies along the length of the member.

Clause 9. The device of Clause 7, wherein the plurality of filaments are braided together.

Clause 10. The device of Clause 7, wherein the plurality of filaments are woven together.

Clause 11. The device of Clause 7, wherein the member is configured such that the filaments form a flat tubular member.

Clause 12. The device of Clause 11, wherein the filaments of the tubular member have a variable pitch.

Clause 13. The device of any one of the preceding clauses, wherein the elongate member comprises at least one slit.

Clause 14. The device of Clause 13, wherein the at least one slit extends along the longitudinal axis of the member.

Clause 15. The device of Clause 13, wherein the elongate member comprises a plurality of slits extending along the longitudinal axis of the member and spaced apart in a substantially linear configuration.

Clause 16. The device of any one of the preceding clauses, wherein the first and second side edges comprise a plurality of wing elements extending laterally therefrom.

Clause 17. The device of Clause 16, wherein the wing elements extend from opposing sides of the elongate member.

Clause 18. The device of Clause 17, wherein a pair of wing elements extend from opposing sides at a first longitudinal position along the member.

Clause 19. The device of Clause 17, wherein the wing elements comprise first and second sets of wing elements, the first set extending from a first side of the member and the second set extending from a second side of the member at different longitudinal positions than the first set.

Clause 20. An occlusive device for occluding a target area, comprising: a elongate member comprising a plurality of filaments, the member having a central backbone and a plurality of wing elements extending from the backbone, the member having (i) a collapsed configuration in which the wings are curled toward the backbone about a longitudinal axis of the member, and (ii) an expanded configuration in which the backbone forms a series of loops.

Clause 21. The device of Clause 20, wherein the wing elements extend from opposing sides of the elongate member.

Clause 22. The device of any one of Clauses 20-21, wherein the wing elements comprise first and second sets of wing elements, the first set extending from a first side of the member and the second set extending from a second side of the member at different longitudinal positions than the first set.

Clause 23. The device of any one of Clauses 20-22, wherein the elongate member comprises a flat, braided tubular member.

Clause 24. The device of any one of Clauses 20-23, wherein the wings uncurl away from the backbone in the expanded configuration.

Clause 25. A method of operating an occlusive device assembly, comprising: advancing an elongate member in a collapsed configuration within a catheter, the member having opposing first and second side edges extending longitudinally along the member, the first and second side edges being curled toward each other about a longitudinal axis of the member in the collapsed configuration; and urging a distal end of the member beyond the catheter distal end to release the member to an expanded configuration in which the first and second side edges move away from each other and the member curls into a series of loops.

Clause 26. The method of Clause 25, further comprising positioning the catheter distal end at an ostium of an aneurysm, wherein the urging comprises urging the member into a fundus of the aneurysm.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present inventions may be disclosed or shown in the context of aneurysm therapy, such embodiments can be used in other occlusive therapies within the vasculature. Furthermore, various applications of such embodiments and modifications thereto, which may occur to those who are skilled in the art, are also encompassed by the general concepts described herein.

In accordance with an aspect of some embodiments disclosed herein, occlusive devices and methods of use are provided that provide advantages over, for example, the use of a traditional coil, a stent, or a braided structure, whether alone or in combination, in occluding an aneurysm. Some embodiments can provide a greater aneurysm surface contact than traditional coils, which can allow less device material to be deployed while tending to increase the surface area of the implanted occlusive device, which can result in increased thrombogenicity. Likelihood of aneurysm recanalization can be greatly reduced through some embodiments, which can provide excellent wall apposition and neck coverage. Further, some embodiments can also be easier to manipulate within the aneurysm dome or cavity. For example, the device can more easily conform to the interior shape of the aneurysm cavity. Furthermore, when an aneurysm begins to reduce in size, aspects of some embodiments allow the device to be deformable such that the device can be compressed or collapse in size to promote healing of the aneurysm, which may not generally possible using traditional coils or other devices.

Figure 1:
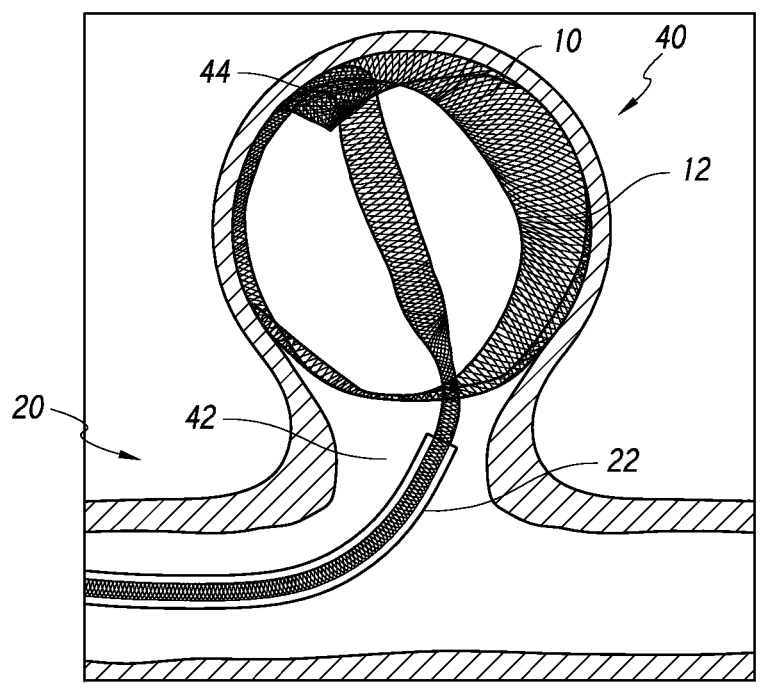
FIG. 1 is a side cross-sectional view illustrating deployment of a device into an aneurysm, according to some embodiments.

For example, FIG. 1 is a side cross-sectional view illustrating deployment of a device into an aneurysm, according to some embodiments. As shown, a device 10 can be advanced to a target aneurysm 40 using a device assembly 20. The device 10 can be advanced from a catheter 22 of the assembly 20 and through a neck 42 of the aneurysm 40 toward a fundus 44 of the aneurysm 40.

The device 10 can comprise a body 12, which can have an elongate shape. In some embodiments, the body 12 can be disposed in a first configuration when positioned within the catheter 22 and expand to a second configuration when released from the catheter 22 into the aneurysm 40. For example, in some embodiments, the first configuration can be achieved when the body 12 is constrained within the catheter 22 and curled or rolled primarily in a direction transverse to a longitudinal axis of the body 12. In some embodiments, the second configuration can be achieved when the body 12 is released from the catheter 22 and curled or rolled primarily in a direction along the longitudinal axis of the body 12. Thus, as the body 12 of the device 10 is released from the catheter 22, a primary curl or roll of the device 10 can transition from one direction along the longitudinal axis to the other, such that the device morphs from an elongate, substantially tubular configuration to a bundled, rounded shape within the aneurysm 40. As the device 10 is released, the body 12 can contact incrementally more of the aneurysm wall and cover more of the neck 42 of the aneurysm 40 until the neck 42 is substantially covered or blocked. Eventually, whether a single or multiple devices are inserted into the aneurysm 40, the wall of the aneurysm can be more completely contacted by device(s) and the volume of the aneurysm 40 can be substantially packed or filled such that circulation or fluid movement is slowed or stopped within the aneurysm 40 and in to the aneurysm 40 through the neck 42 is substantially slowed or stopped.

Figure 2A:
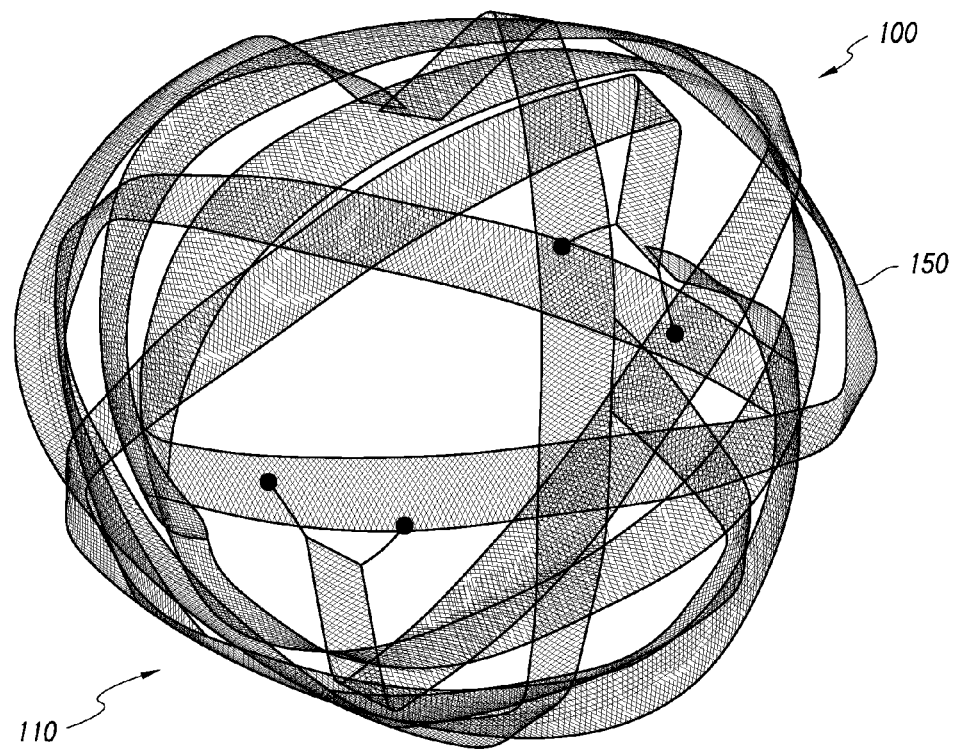
FIG. 2A is a perspective view of an occlusive device that can be released into a target area of a body lumen, according to some embodiments.

FIG. 2A depicts an embodiment of an occlusive device 100 that can be released into a target area of a body for occluding the target area. The target area can be a body lumen or space, such as aneurysms, including neurovascular or intracranial aneurysms, blood vessels, or other hollow anatomical structures. According to some embodiments, the device 100 can provide numerous and distinct advantages over other occlusive devices, such as coils and expandable filamentary structures, including stents, wire cages, and other known occlusive devices.

For example, in the case of aneurysm therapy, the device 100 can pack or fill a target volume and accommodate the shape of the target volume, functions which stent or braided structures may not adequately perform on their own. Further, the device 100 can contact an irregular sidewall shape of the aneurysm. Furthermore, the device 100 can also maximize coverage of the aneurysm neck, adequately grip the sidewall of the aneurysm to prevent device herniation or slippage, promote a healing response along the aneurysm neck, provide predictable expansion to a desired expanded shape, and achieve these ends without requiring other framing or neck blocking devices, functions which coil structures may not adequately perform on their own.

Figure 3A:
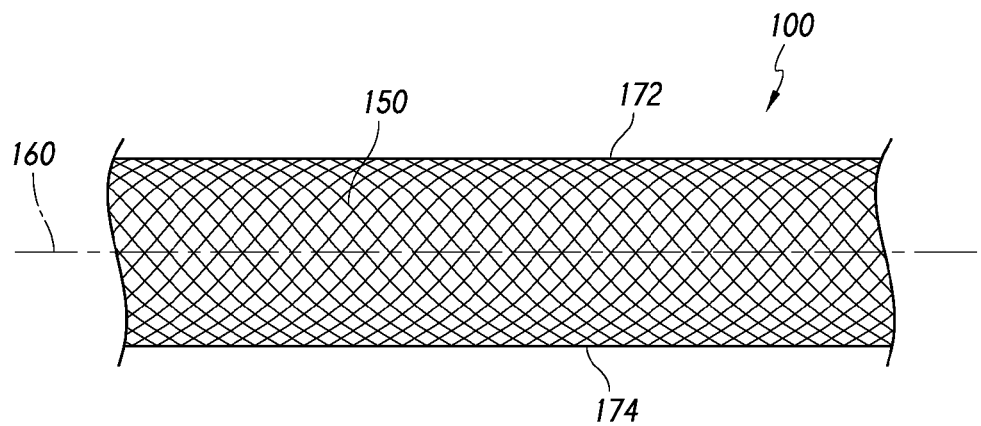
FIGS. 3A-3I illustrate aspects and optional features that can be incorporated into the device, according to some embodiments.

Referring to FIG. 3A, The device 100 is illustrated as comprising a body, ribbon, or elongate member 150 formed from a braid having a number of strands, such as metallic wires or polymeric filaments. For example, the body 150 can comprise nitinol or other suitable (superelastic)? materials. For example, in accordance with some embodiments, the material of which the body 150 is constructed can permit the body 150 to be substantially straight (and relatively elongated, for example, in the second configuration for delivery) while at or near room temperature and coiled (and relatively shortened or looped, for example, in the first configuration for space packing or filling in the target area) while at or near human body temperature. However, in some embodiments, the device 100 can also comprise other types of materials or configurations of material. For example, the device 100 can comprise a bioresorbable material or polymer. Further, the material can also comprise cobalt chromium.

Further, the device 100 can comprise a woven, knit, braided, or a non-braided, non-knit, and non-woven, single, continuous piece of material, or molded pieces, whether in a flat sheet or tubular configuration. The device 100 can comprise a single or multi-layer sheet or tubular structure. In some embodiments, the device 100 can comprise a laser-cut or photo-etched material. The device 100 can also comprise a material formed from one or more non-woven fibers, e.g., long fibers, which are pressed or otherwise bonded together into a tubular or flat sheet configuration.

In some embodiments, the device 100 can be configured as a tubular structure, which can be flattened to provide a generally flat cross-sectional profile. The flattening of the tubular structure can thus provide a multi-layer sheet or structure whose layers are, incidentally, connected along the lateral longitudinal edges of the device.

In some embodiments, the device 100 can comprise a flat sheet, which can be folded onto itself one or more times along the longitudinal axis of the device 100. The folding of the material can thus provide a multi-layer sheet or structure. The use of such a sheet of material can provide ease of manufacturing and enable greater control of the ends of the device 100.

In some embodiments, regardless of the material or configuration of the device 100, the device 100 can comprise a body that has a textured surface or a smooth surface. For example, in some embodiments, the device can comprise a body that has an irregular, porous, dimpled, braided, woven, or knitted surface. Thus, some embodiments of the device 100 can be configured to provide pores, apertures, indentations, or interstitial spaces that impart a desired level of thrombogenicity and/or resistance to blood flow. Further, such pores, apertures, indentations, or interstitial spaces can advantageously engage the sidewall of the aneurysm while being released into the aneurysm. As such, during deployment of the device 100, a textured surface can tend to enhance wall apposition and ensure that the device 100 engages with the aneurysm wall and does not move within or herniate from the aneurysm.

Further, instead of or in addition to such a textured surface, thrombogenic materials can be employed as coatings, additives or otherwise in the device 100, for example gold, platinum, platinum-iridium alloy, or fibrin. Where a braid is employed, the braid wire metals may be selected to maximize the electrical currents (and any resulting thrombogenicity).

Figure 2B:
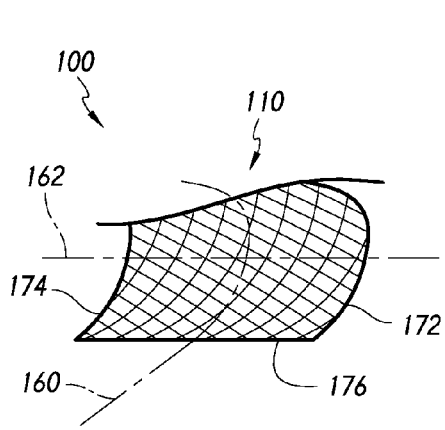
FIG. 2B is a perspective, cross-sectional view of the device along its longitudinal axis, wherein the device is in a first, expanded configuration that can be achieved upon expansion within the target area, according to some embodiments.

In use, the device 100 shown in FIG. 2A can be loaded into a delivery system, such as a catheter, and delivered to a target area within the body. According to some embodiments, when released from the delivery system in the target area, the device 100 can assume an expanded, first, or primary configuration 110, as shown in FIGS. 2A-2B. However, when the device 100 is being delivered to the target area, can also have a collapsed, second, or secondary configuration 120, such as that shown in the embodiment in FIG. 2C. Thus, to facilitate delivery of the device 100, the body 150 can be positioned in a configuration such as the collapsed configuration 120 when in a delivery catheter. Upon being released from the delivery catheter, the body 150 can preferentially assume the expanded configuration 110. Accordingly, when unconstrained, the body 150 may tend to self-adjust or move to the expanded configuration 110 (as opposed to staying in or moving to the collapsed configuration 120).

In the expanded configuration 110 shown in FIGS. 2A-2B, a body 150 of the device 100 can be looped, curved, curled, or rolled about an axis that is transverse to a longitudinal axis 160 of the body 150. Further, in the collapsed configuration 120 shown in FIG. 2C (e.g., achieved when the device 100 is in a catheter), a body 150 of the device 100 can be looped, curved, curled, or rolled about an axis that is aligned with a longitudinal axis 160 of the body 150.

In some embodiments, the body 150 can comprise a "curl vector" 162 that can be geometrically defined, using the "right-hand rule," as the resulting vector or direction in which the thumb points when the fingers of the hand are curled along the same arc or orientation of the body 150. As shown in FIG. 2B, when in the expanded configuration 110, the curl vector 162 can be oriented substantially transverse relative to the longitudinal axis 160 of the body. In some embodiments, the curl vector 162 can extend in a generally perpendicular direction relative to the longitudinal axis 160 when the body 150 is in the expanded configuration 110.

For example, the body 150 can comprise opposing first and second side edges 172, 174. In the expanded configuration 110, at a given point along the longitudinal axis 160, the first and second side edges 172, 174 can be spaced apart at a first distance. Additionally, as shown FIG. 2B, the device 100 can comprise a leading edge 176 (which can represent a cross-section of the device that is substantially perpendicular to the longitudinal axis 160), which can have a substantially flat cross-sectional shape when the device 100 is in the expanded configuration 110.

Figure 9A:
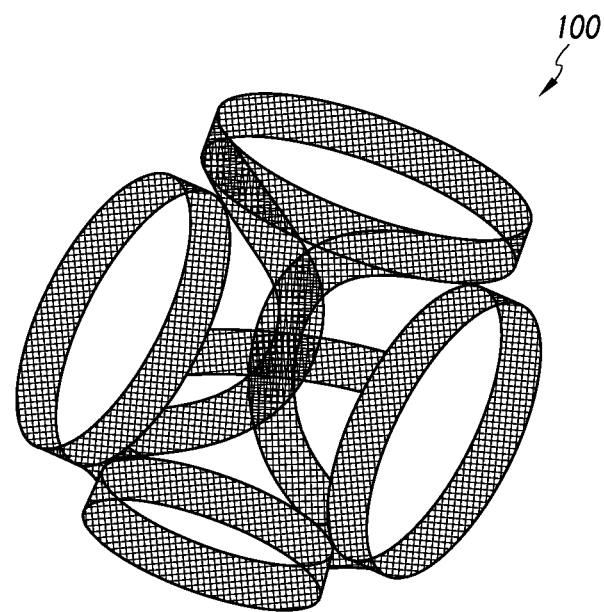
FIGS. 9A-9B illustrate additional shapes of a device in an expanded configuration, according to some embodiments.
Figure 9B:
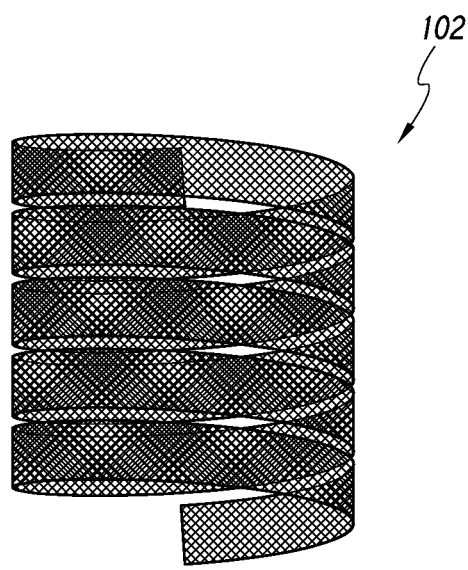

The device 100 can substantially pack or fill the internal volume of the body lumen, such as an aneurysm, after being released from a delivery system. For example, as discussed further below, when the device 100 is in the expanded configuration 110, the device 100 can comprise a variety of three-dimensional shapes, including spherical or non-spherical shapes, including, hemispheres, noodles, coils, prolate spheroids, oblate spheroids, bowls, non-spherical surfaces of revolution (e.g., toruses, cones, cylinders, or other shapes rotated about a center point or coplanar axis), and/or combinations thereof. For example, FIG. 2A illustrates an embodiment of the device having a ball-shaped or substantially spherical configuration while FIGS. 9A-9B illustrate embodiments of a device 100 having a semi-cylindrical, 3-D, or cylindrical configurations.

Figure 2C:
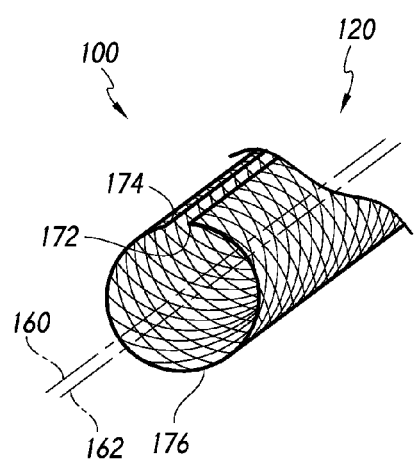
FIG. 2C is a perspective, cross-sectional view of the device along its longitudinal axis, wherein the device is in a second, collapsed configuration that can be maintained during advancement to the target area, according to some embodiments.

However, in the collapsed configuration 120, illustrated in FIG. 2C, the body 150 can have a substantially cylindrical configuration. For example, the body 150 can be curved, curled, or rolled around or about a line substantially parallel relative to the longitudinal axis 160. As shown in FIG. 2C, when in the collapsed configuration 120, the body 150 can be curled such that the curl vector 162 can be oriented substantially parallel relative to the longitudinal axis 160 of the body. When the body 150 is in the collapsed configuration 120, even though the curl vector 162 may not be substantially parallel relative to the longitudinal axis 160, the curl vector 162 can be within about 30°, within about 20°, or within about 10° of parallel relative to the longitudinal axis 160. Further, in the collapsed configuration 120, the first and second side edges 172, 174 can be curled toward each other.

For example, as noted above, in the expanded configuration 110, at a given point along the longitudinal axis 160, the first and second side edges 172, 174 can be spaced apart at the first distance. When moved to the collapsed configuration 120, at a given point along the longitudinal axis 160, the first and second side edges 172, 174 can be spaced apart at a second distance, which is less than the first distance. Additionally, as shown FIG. 2C, the leading edge 176 of the device 100 (which can represent a cross-section of the device that is substantially perpendicular to the longitudinal axis 160) can have a curved shape or cross-section when the device 100 is in the collapsed configuration 110.

In some embodiments, the first and second side edges 172, 174 can be substantially parallel relative to each other in the collapsed configuration 120. For example, the first and second side edges 172, 174 can extend substantially parallel relative to the longitudinal axis 160. In some embodiments, the first and second side edges 172, 174 can also extend at least partially helically about the longitudinal axis 160 in the collapsed configuration 120.

During delivery of the device 100, although curled or rolled about the longitudinal axis 160 in the collapsed configuration 120, the first and second side edges 172, 174 may slightly deflect, bend, or curve onto the longitudinal axis 160 while passing through tortuousities of the vasculature. For purposes of this disclosure, such motion is considered typical during advancement of the device 100 to the target area and when device 100 is positioned in the collapsed, second configuration 120 within the catheter, the device 100 is considered to be in the collapsed configuration 120 regardless of the degree or amount of curving or looping of the device 100 onto the longitudinal axis 160.

Advantageously then, some embodiments can provide a device that is sufficiently flexible to bend or deflect while advancing through tortuosities of the vasculature without kinking or breaking fibers or filaments of the device. Further, some embodiments also allow the device 100 to be subjected to substantial pushing forces without collapsing or buckling. For example, some embodiments allow the device to be positioned in a generally tubular or rolled shape, thus advantageously increasing the strength of the device when under axial compression in the collapsed configuration.

As noted above, in accordance with some embodiments, the body 150 of the device 100 can be configured to have at least one preset configurations. For example, the body 150 of the device 100 can be biased such that the device 100 assumes a first preset two or three-dimensional configuration in the expanded configuration 110. However, in some embodiments, the body 150 of the device 100 can also comprise a second preset configuration in which the device 100 assumes the collapsed configuration 120.

In some embodiments, the body 150 of the device 100 can be biased toward one or both of the first or second preset configurations. The device 100 can also be preset to assume the first configuration as a primary configuration and to assume the second configuration is a secondary configuration. For example, the body 150 of the device 100 can have dual stable positions. Optionally, the first configuration can be preferred when no external forces are being exerted upon the body 150.

Further, some embodiments can be provided in which the device has only one or both of these preset configurations.

For example, in some embodiments, although the body 150 of the device 100 may have only a preset expanded configuration 110, the device 100 can be rolled or curled sufficiently to permit loading and advancement of the device 100 within a catheter. Further, in some embodiments, although the body 150 of the device 100 may have only a preset collapsed configuration 120, the device 100 can incorporate another structure, such as the tensioning member discussed below, to impart a two or three-dimensional shape to the device 100.

FIGS. 3A-3I show top views of various embodiments of an occlusive device in a planar or flat configuration, for purposes of illustration. Any of the devices illustrated in FIGS. 3A-3I can be formed using a tubular mesh material that is flattened into a two-layer sheet. However, any of the devices illustrated in FIGS. 3A-3I can also be configured as a single layer sheet of mesh material, which can be folded once, twice, or more times, or not at all in forming the device. Cross-sectional profiles of some embodiments are illustrated in FIGS. 5A-6B. Further, in accordance with some embodiments, the device, whether formed from a flattened tubular mesh or a single layer sheet (folded or not), can optionally comprise one or more features, such as slits or protrusions that can facilitate access through the device or increase the coverage of the device in its expanded configuration. Other features can also be optionally incorporated into the device to provide radiopacity to the device, a drug delivery means, swellable materials, or other features such as those disclosed herein or known in the art.

For example, FIG. 3A illustrates a section of the device 100 in which the body 150 is configured such that the first and second edges 172, 174 are substantially straight or extend substantially parallel relative to the longitudinal axis 160 of the device 100.

Figure 3B:
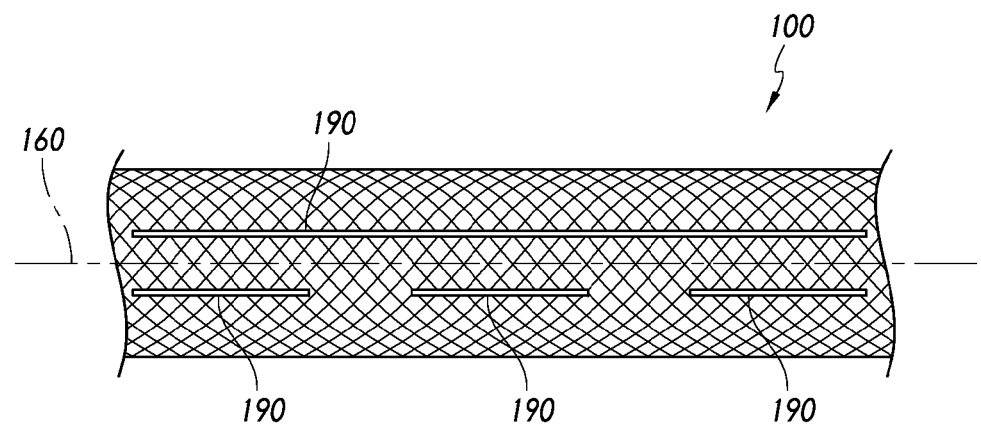

FIG. 3B illustrates that the device 100 can optionally comprise at least one longitudinal slit. As shown, the device 100 can comprise at least one slit 190 extending along the longitudinal axis 160 of the device 100. In some embodiments, the device 100 can comprise a plurality of slits 190, such as that shown in FIG. 3B. The slit 190 can permit the clinician to advance or inject another embolic device, such as one or more coils or an embolic material or liquid, into the aneurysm. For example, a suitable liquid embolic is the Onyx™ liquid embolic system manufactured by Covidien LP, Irvine, Calif. Onyx™ liquid embolic system is a non-adhesive liquid used in the treatment of brain arteriovenous malformations. Onyx™ liquid embolic system is comprised of an ethylene vinyl alcohol ("EVOH") copolymer dissolved in dimethyl sulfoxide ("DMSO"), and suspended micronized tantalum powder to provide contrast for visualization under fluoroscopy. Other liquid embolic solutions are also envisioned.

Figure 3C:
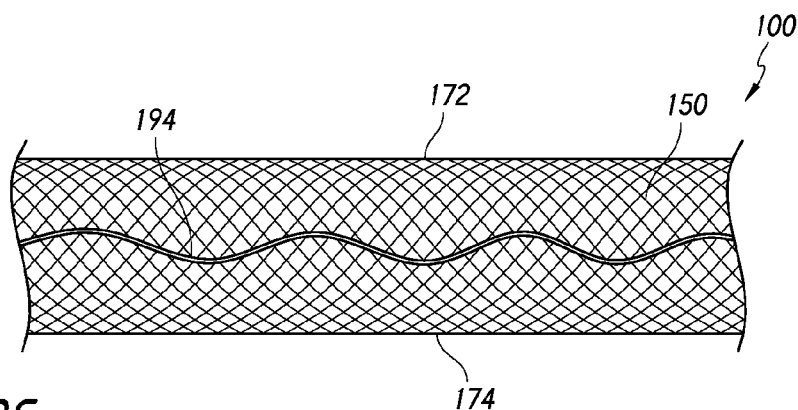

FIG. 3C illustrates that in some embodiments, the device 100 can optionally comprise a shape-imparting, structural, or tensioning member 194. The body 150 can be formed separately from the tensioning member 194 such that the tensioning member 194 acts as a separate, independent component that influences the shape of the body 150. As shown in FIG. 3C, the tensioning member 194 can be interwoven into the braid.

The tensioning member 194 can be coupled to one or more sections of the device 100 in order to provide stretch resistant or anti-stretch properties to the device 100. Thus, in some embodiments, although the device 100 can be formed from a resilient or deformable material, the incorporation of the tensioning member 194 can ensure that the length of the device 100 varies only slightly or is substantially unchanged during advancement of the device 100 through the delivery system and during expansion of the device 100 within the target area. Further, in some embodiments, the tensioning member 194 can resiliently provide stretch resistance. Thus, the length of the device 100 can increase and the tensioning member 194 can resist the stretching and urge the device 100 toward its unstretched, original length.

In some embodiments, the tensioning member 194 may not only provide anti-stretch capabilities, but can also impart a two or three-dimensional configuration to the device 100 when in the expanded configuration 110. The tensioning member 194 may be employed to impart any of the two or three-dimensional configurations discussed herein, or other suitable such configurations.

A desired unconstrained configuration can be heat-set or otherwise processed into the tensioning member 194. The tensioning member 194 can be employed with a device 100 which itself has no particular heat-set or otherwise preset unconstrained configuration, or with a device 100 which does have a preset two or three-dimensional configuration. Where only the tensioning member 194 has a preset unconstrained configuration, the tensioning member 194 can urge the device 100 into a two or three-dimensional unconstrained or semi-constrained configuration upon release from a delivery catheter or into the target area. The unconstrained configuration thus achieved by the device 100 can be generally similar to the unconstrained configuration that is preset in the tensioning member 194.

The tensioning member 194 can comprise first and second ends, with at least one of the ends being coupled to the body 150 of the device 100. In some embodiments, the tensioning member 194 can comprise first and second ends that are each coupled to respective first and second portions of the device 100. The first and second portions of the device 100 can comprise first and second end portions.

The tensioning member 194 can facilitate delivery of the device 100 by providing either a pulling or pushing function during advancement of the device 100. For example, in some embodiments, the tensioning member 194 can be coupled at one end to only one portion or end of the device 100. In such embodiments, the other end of the tensioning member 194 can be grasped or coupled to a portion of the delivery system for providing anti-stretch properties. As such, the device 100 can be delivered within a catheter using a core wire or assembly that comprises a pad or engagement member at its distal end. The engagement member of the core wire can engage the device 100 at a point distal to a proximal end of the device 100. In some embodiments, the engagement member can engage the device 100 at a point proximal to the distal end of the device 100, such as at a midpoint along the longitudinal axis of the device 100, or between the midpoint and the distal end of the device 100. The tensioning member 194 can be coupled to the proximal end of the device 100 and extend distally such that a distal end of the tensioning member 194 is engaged with a portion of the core wire, such as the engagement member. In some embodiments, the distal end of the tensioning member 194 can be frictionally engaged between the engagement member and the device 100 or otherwise releasably engaged with the core wire. Further, in some embodiments, the tensioning member 194 can be attached to a distal end of the core wire or engagement member and a proximal end of the device 100 and be configured to dissolve upon release of the device 100 within the target area.

Alternatively, in accordance with some embodiments, the tensioning member 194 can provide column strength to the device 100. Thus, the tensioning member 194 may be used to urge the device 100 distally through the catheter during delivery of the device 100 by manually pushing a proximally extending portion of the tensioning member 194 in a distal direction. For example, the tensioning member 194 can be coupled to a distal end portion of the body 150 of the device 100 and a proximal end of the tensioning member 194 can be contacted (and some embodiments, along with a proximal end of the body 150) to push the device 100 distally through a catheter lumen. As such, some embodiments of the delivery system can be configured to abut or the coupled to a proximal end of the tensioning member 194 for pushing the device 100 through the catheter.

In addition, similar to the body 150 of the device 100, the tensioning member 194, which can be formed separately from the body 150, may comprise one or more nitinol wires, which can be pre-shaped as discussed above. For example, nitinol or AUSTENITIC nitinol (or other material) can be employed, which is substantially straight (and relatively elongated) while at or near room temperature and coiled (and relatively shortened) while at or near human body temperature. Such a tensioning member can be used as discussed above to maintain an axial length of the device 100 during delivery through a catheter lumen, but permit or facilitate movement from the collapsed configuration 120 to the expanded configuration 110. Further, as noted above, some embodiments can be provided in which the tensioning member 194 imparts a two or three-dimensional shape to the device 100 upon release from the catheter.

Figure 3D:
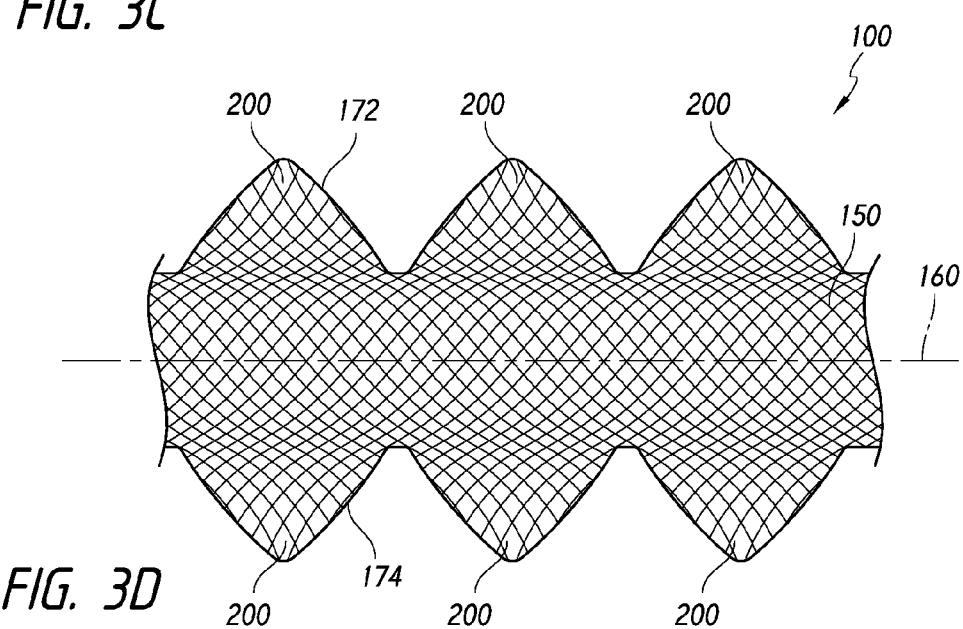
Figure 3E:
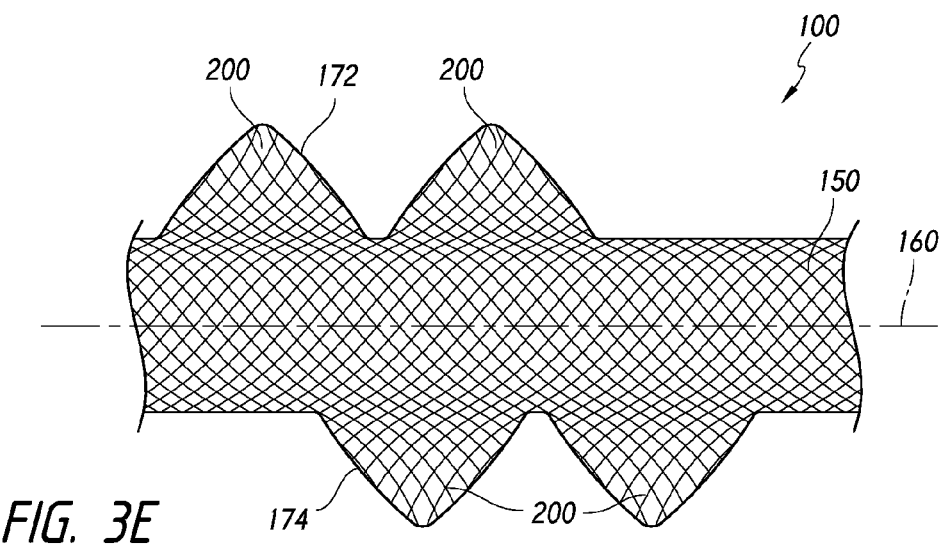

Referring now to FIGS. 3D-3E, the body 150 of the device 100 can be configured such that the edges 172, 174 converge or diverge relative to each other. For example, as shown in FIG. 3D, the body 150 can comprise one or more enlarged portions, which can comprise wings, bulges, that extend laterally outward from the longitudinal axis 160 of the body 150.

Figure 3F:
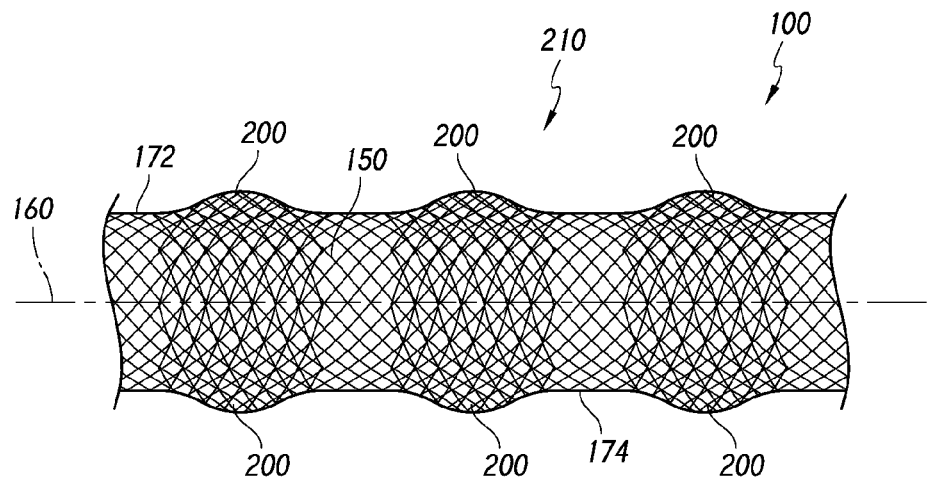
Figure 3G:
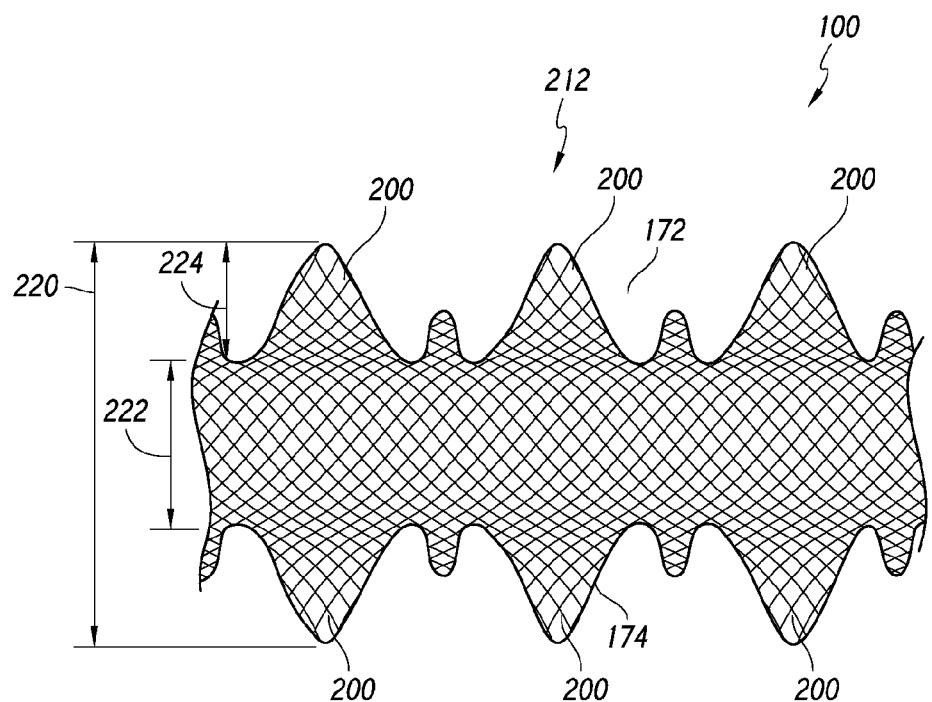

FIG. 3D illustrates a plurality of enlarged portions 200 that extend generally symmetrically from opposing sides of the device 100. Further, FIG. 3E illustrates another embodiment of the device 100 in which enlarged portions 200 extend in a staggered configuration from opposing sides of the device 100. Furthermore, FIG. 3G illustrates another embodiment in which the enlarged portions 200 have different widths or sizes.

The shape and dimensions of the enlarged portions 200 can, as illustrated, provide the enlarged portions 200 with a rounded, semicircular edge. However, the enlarged portions or wings 200 can also be configured such that the edges 172, 174 have a sinusoidal shape. The enlarged portions can comprise any shape, size, or occupy any position along the length of the device, and any combinations thereof.

The enlarged portions 200 can be formed from a single, continuous piece of material with the body 150. The body 150 can be cut or otherwise shaped to include the enlarged portions 200. For example, the body 150 can be formed from a braided sheet or tube whose filaments are stretched laterally and heat-set to form the enlarged portions 200. However, in some embodiments, the enlarged portions 200 can be formed separately from and subsequently coupled to the body 150.

Further, the enlarged portions 200 can be configured to roll or curl about the longitudinal axis 160 or to laterally self-expand from a compressed configuration. The embodiments illustrated in FIGS. 3D-3E illustrate rollable or curlable enlarged portions 200. Further, FIGS. 3F-3G illustrate embodiments of the device 100 in which the enlarged portions 200 are in respective compressed and expanded positions 210, 212. When compressed or prior to contact with the fluid or heat, the enlarged portions 200 can cause the pic count (i.e., the count of the per-inch-crossings of filaments or pics-per-inch (PPI)) or fiber density along those portions of the body 150 to be higher where the enlarged portions 200 are disposed. When released or exposed to a fluid or heat, the enlarged portions 200 can move from the compressed position 210 to the expanded position 212, as shown in FIGS. 3F-3G. For example, in some embodiments, the enlarged portions 200 can be superelastic.

For example, when the enlarged portions 200 are released (such as by uncurling, unrolling, or expanding from the collapsed position), the edges 172, 174 along the enlarged portions 200 can be spaced apart greater than the edges 172, 174 along the body 150. The edges 172, 174 can have a maximum width (for example, measured at a distance 220 in FIG. 3G) and a minimum width (for example, measured at a distance 222 in FIG. 3G). The maximum width 220 can be greater than the minimum width 222. In some embodiments, the maximum width 220 can be from about 1.1 to about 4 times as large, from about 1.5 to about 3.5 times as large, from about 2 to about 3 times as large, or from about 2.2 to about 2.8 times as large as the minimum width 222. In some embodiments, the maximum width 220 may not exceed more than three or four times the minimum width 222.

Further, in some embodiments, as shown in FIG. 3G, the enlarged portion or wing 200 can comprise a width 224 that is approximately equal to the minimum width 222. Furthermore, and some embodiments, the width 224 of the enlarged portion or wing 200 can be between about 0.25 and about 2 times, about 0.5 to about 1.5 times, about 1 and about 1.25 times the minimum width 222.

In accordance with some embodiments, the enlarged portions 200 can be configured to have different widths, sizes (e.g., longitudinal lengths), or shapes along the length of the device 100. Thus, when released, the edges 172, 174 can define a generally irregular pattern. The maximum and minimum widths 220, 222 can be within the range, such as those discussed above.

Additionally, when released, the enlarged portions 200 can be configured to provide a fiber density or pattern that is substantially equivalent or identical to the fiber density or pattern of the body 150. However, the enlarged portions 200 can also be configured to provide a lower fiber density or different pattern than portions of the body 150 disposed adjacent to the respective enlarged portion or wing 200. In such embodiments, the enlarged portions 200 can be heat-set or otherwise pre-shaped in such a configuration.

As noted above, the enlarged portions 200 can be formed by stretching the body 150 to widen it at discrete locations along its length or by coupling a separate component to the body 150. In embodiments in which the enlarged portions 200 move between compressed and expanded positions, the enlarged portions 200 can be maintained in the compressed position by exertion of a compressing force or by the use of a coating on the device 100, which can assist in maintaining the compressed position until the coating dissolves in the presence of fluid after release.

Figure 3H:
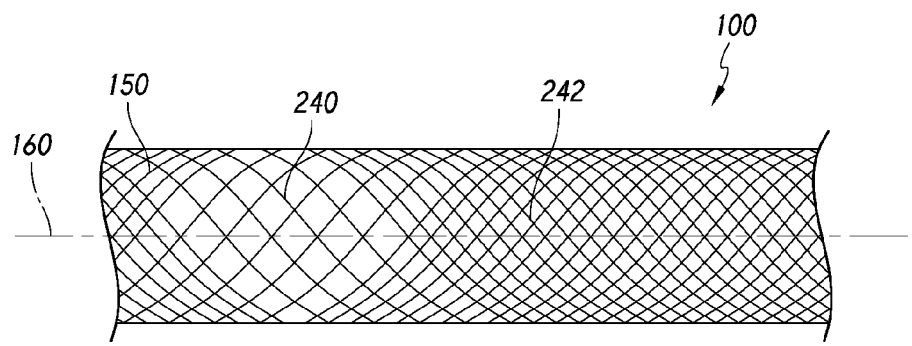

Referring now to FIG. 3H, in accordance with some embodiments, the body 150 can comprise first and second sections 240, 242 that can have different properties. For example, the body 150 can be configured such that a braid, weave, or knit pattern changes at least once or more or varies along the length of the body 150. In some embodiments, the body 150 can comprise a braided structure that comprises first and second sections 240, 242. The first and second sections 240, 242 can have different porosities, pic counts, filament pitch, filament size, or braid/weave/knit densities.

Thus, the first and second sections 240, 242 can have different properties that can advantageously affect the function of the device 100 within the target area and during delivery to the target area.

For example, a higher pic count or braid density can tend to reduce or block flow through the device 100, while a lower pic count or braid density can permit flow or injection of embolic materials or coils through the device 100. Additionally, the pic count or braid density can also influence the frictional engagement with the target area wall and endothelialization when released, for example, at the neck of an aneurysm. Further, the pitch or alignment of the filaments can also affect longitudinal compressibility or pushability when urging the device 100 distally within the catheter toward the target area. For example, the fibers can be closely axially aligned with the longitudinal axis of the device 100, thus enhancing or increasing pushability of the device 100. Furthermore, a lower pic count can also tend to increase pushability of the device 100.

Figure 3I:
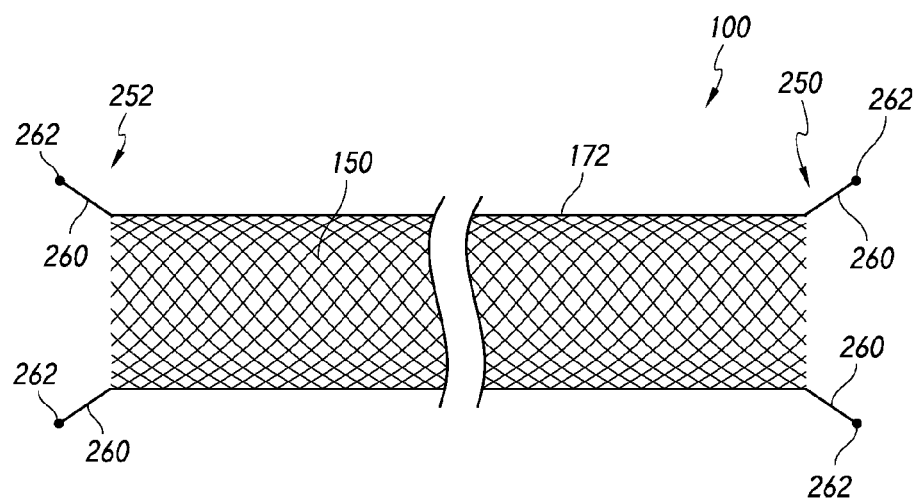

Referring now to FIG. 3I, the device 100 can also be configured such that at least one of the proximal and distal ends 250, 252 of the device 100 comprise an atraumatic feature or component. For example, the device 100 can be configured such that the proximal and/or distal ends 250, 252 comprises one or more points or corners (whether rounded or pointed) having a filament 260 extending therefrom. The filament 260 can allow the proximal and/or distal ends 250, 252 to gently and atraumatically contact the target area wall (such as an aneurysm wall). In some embodiments, the filament 260 can comprise a rounded or ball-shaped tip 262.

FIGS. 4-6B illustrate views of a device assembly 300 in which a device 100 is disposed within a catheter 302. As shown, the device 100 is in the collapsed configuration 120. In the illustrated embodiment, the device 100 comprises enlarged portions 200 that are folded or curled around the longitudinal axis of the device 100. Further, the device 100 also comprises atraumatic portions or filaments 260. Thus, the device 100 can be distally pushed out of the catheter 302 and into a target aneurysm whereat the device 100 can expand from the collapsed configuration 120 to the expanded configuration.

Additionally, in accordance with some embodiments, the device 100 can comprise a radiopaque marker at one or both of its ends, at locations along the length thereof, or along the entire length thereof. Such markers can be configured similar to the filament 260 and/or the rounded or ball-shaped tip 262 thereof. For example, the filament 260 and/or the rounded or ball-shape tip 262 thereof can be radiopaque.

The length of the device 100 can be from about 5 mm to about 250 mm. In some embodiments, the length can be from about 7 mm to about 180 mm. Further, the length can be from about 9 mm to about 100 mm. Furthermore, the length can be from about 10 mm to about 50 mm. The length of the device 100 can also be about 25 mm. As noted below, multiple devices having multiple lengths and/or configurations can also be used.

In some embodiments, the device can be configured such that a wall of the device 100 comprises a flow diverting pore size. A "flow diverting pore size" can refer to an average pore size of pores (in at least a section of a device) that is sufficiently small enough to interfere with or inhibit fluid exchange through the pores of that section.

A device 100 (e.g., at least a proximal section of the device) can have an active section or a flow diverting section with a flow diverting pore size when the pores of the section are sized to inhibit flow of blood through the sidewall into an aneurysm to a degree sufficient to lead to thrombosis and healing of the aneurysm when the tubular member is positioned in a blood vessel and adjacent to the aneurysm.

For example, a flow diverting pore size can be achieved when pores in the flow diverting or active section have an average pore size of less than about 500 microns when the device (e.g., stent) is in the expanded state. In some embodiments, the average pore size can be less than about 320 microns. Further, the average pore size can be from about 25 microns to about 350 microns. The average pore size can also be from about 40 microns to about 200 microns. Further, in some embodiments, the average pore size can be from about 60 microns to about 150 microns. Furthermore, the average pore size can be about 120 microns.

Average pore sizes that are about within such ranges can operate to divert fluid flow and induce thrombosis within the lumen or interior volume enclosed by the wall. The pores can have a pore size that is generally constant. The pores can have an average pore size that is measured using an inscribed circle diameter.

Additionally, in some embodiments, a device 100 can be provided with a porosity in the range of 10%-95% may be employed in the expanded braid to achieve these effects. In some embodiments, a porosity in the range of about 30% to about 90% may be employed to achieve these effects. Further, a porosity in the range of about 50% to about 85% may be employed to achieve these effects. Other various features can be incorporated into the device 100, such as those disclosed in copending International Application No. PCT/US13/33419, filed Mar. 22, 2013, the entirety of which is incorporated herein by reference.

Figure 4:
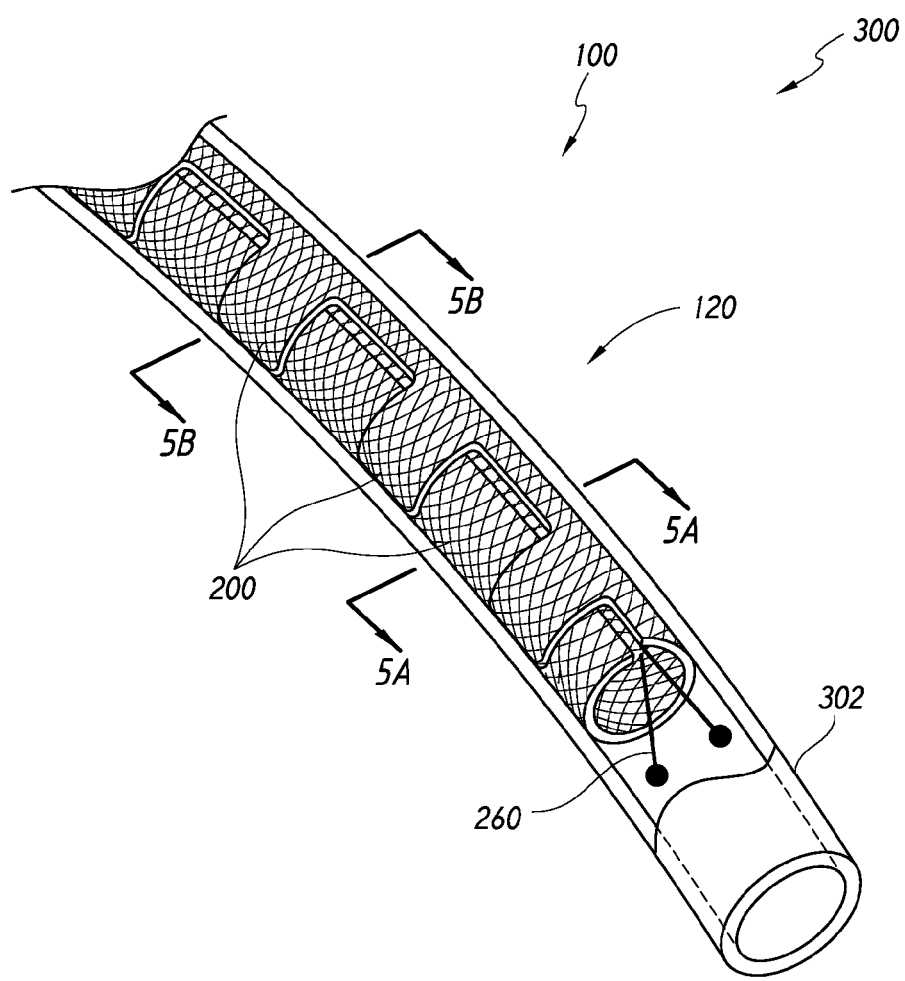
FIG. 4 illustrates a device in a collapsed configuration within a catheter, according to some embodiments.
Figure 5A:
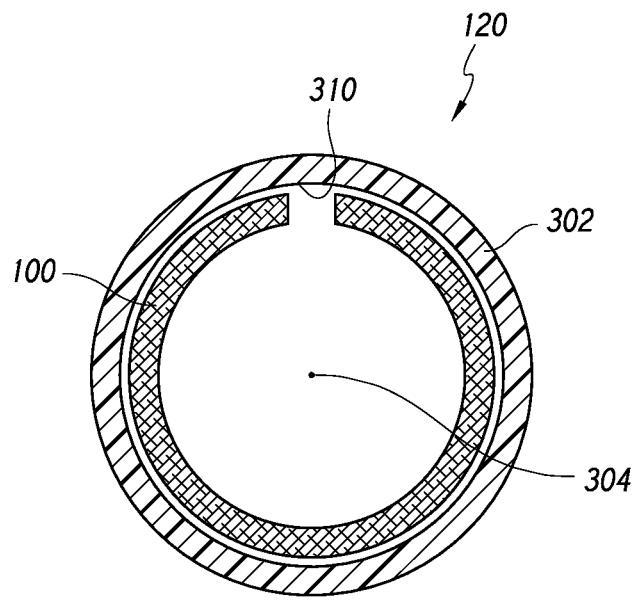
FIGS. 5A-6B illustrate cross-sectional views of a device disposed within a catheter, according to some embodiments.
Figure 5B:
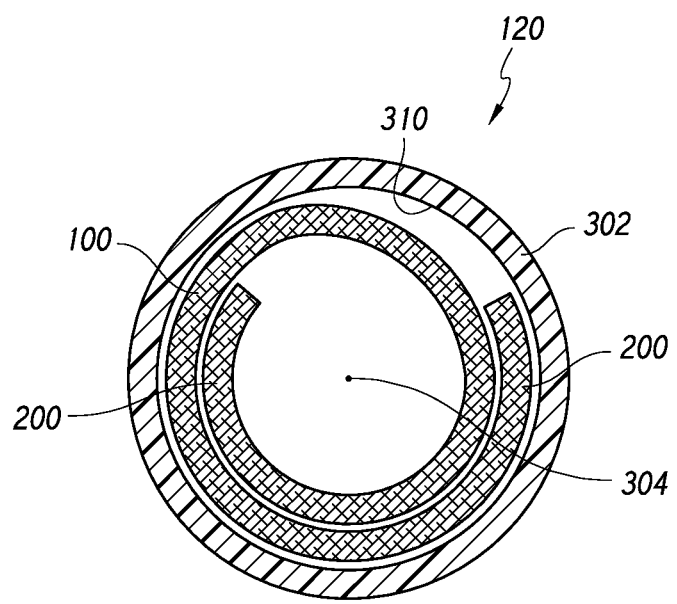

FIGS. 5A-5B illustrate cross-sectional views of the device 100 and catheter 302 taken along section lines 5A-5A and 5B-5B of FIG. 4. Similar to the view illustrated in FIG. 2C, FIGS. 5A-5B illustrate a cross-sectional view of the device 100 in which the device is curved, curled, or rolled around or about a line 304 substantially parallel relative to the longitudinal axis 160 of the device 100.

Figure 6A:
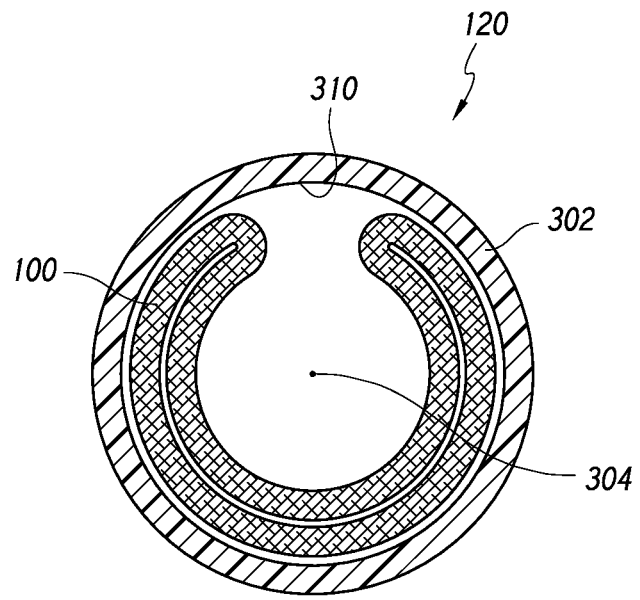
Figure 6B:
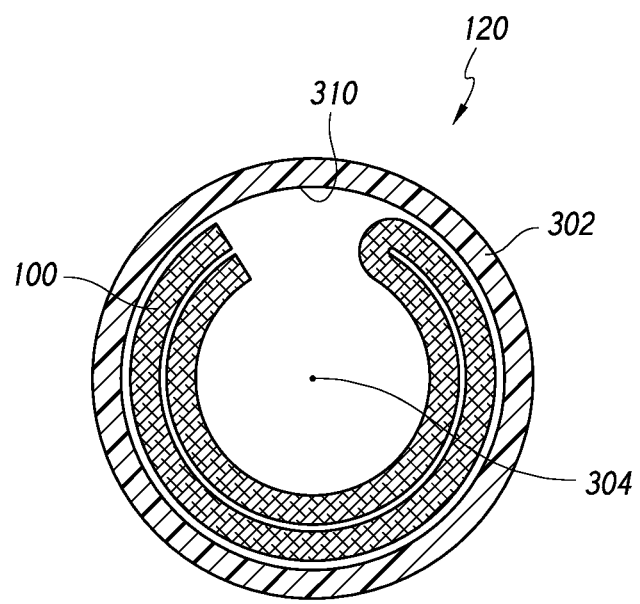

FIGS. 6A-6B also illustrate other embodiments of the device in which the device is folded or compressed from a tubular or sheet configuration. For example, FIG. 6A illustrates that the device 100 can comprise a tubular shape that is flattened and curved, curled, or rolled around or about a line 304 substantially parallel relative to the longitudinal axis 160. Further, FIG. 6B illustrates that the device 100 can comprise a sheet that is folded at least once and curved, curled, or rolled around or about a line 304 substantially parallel relative to the longitudinal axis 160.

In accordance with some embodiments, the device 100 can exhibit improved or high pushability relative to comparable devices or structures by virtue of its collapsed configuration 120. The collapsed configuration 120 can improve pushability by reducing the amount of exposed material in contact with the catheter inner wall and/or by causing the collapse device to contact less than the full circumference of the catheter inner wall.

For example, because the device 100 is in a curved, curled, or rolled shape in the collapsed configuration 120, at least a portion of the device 100 will not come in contact with an interior surface or wall 310 of the catheter 302. In some embodiments, the interior wall 310 can be contacted along less than its full circumference. In its collapsed configuration 120, the device 100 will require much less pushing force than comparable structures that are otherwise simply radially collapsed or compressed from an expanded diameter to a compressed diameter (thereby either increasing the braid density or the axial length of the device in the collapsed state), as is typical with stents and other braided structures, such as braid balls.

For example, with reference to FIG. 5B, the device 100 can be rolled onto itself such that a cross-sectional inner portion of the device is radially within a cross-sectional outer portion of the device. The cross-sectional inner portion of the device can be, for purposes of this disclosure, considered as the rolled portion of the device that is radially overlapped by another portion of the device. As such, only the cross-sectional outer portion of the device will contact the inner wall 310 of the catheter 302.

Further, as illustrated in FIGS. 5A and 6A-6B, in some embodiments, the curled device 100 can extend along less than the entire circumference of the inner wall 310 of the catheter 302. As shown, in its folded or compressed, flattened cross-sectional configuration (which can be assumed in the expanded configuration, as illustrated in FIG. 2B), a cross-sectional width of the device 100 can be less than the circumference of the inner wall 310.

Accordingly, depending on the size of the catheter to be used, which can vary from about 3 Fr to about 8 Fr, the device 100 can be flattened or folded, and in some embodiments, rolled onto itself. When the device is not rolled onto itself (e.g., before insertion into the catheter), the width of the flattened cross-section can be between about 3 mm and about 7 mm, between about 4 mm and about 6 mm, or about 5 mm. Such dimensions can be used for single layer or multi-layer flattened cross-sections.

The device can be formed from a flat sheet. For example, if folded into two substantially equal sections before being rolled and inserted into a catheter, the flat sheet can have a width of between about 6 mm and about 14 mm, between about 8 mm and about 12 mm, or about 10 mm. Similar metrics can be followed when the device is formed using a folded sheet that has a trifold cross-section.

When the device is rolled onto itself, the cross-sectional diameter of the rolled, flattened material can be between about 1 mm and about 4 mm, between about 1.5 mm and about 3.5 mm, or between about 2 mm and about 3 mm. The cross-sectional diameter of the device, when rolled onto itself, can also tend to depend on the ability of the material to roll up in a delivery tube or catheter (e.g., its bending strength).

Thus, the collapsed configuration 120 of the device 100 can allow a greater amount of material or device to be advanced through the catheter 302 while minimizing the frictional resistance between the device 100 and catheter wall 310. As a result, the pushability of the device 100 can be advantageously improved.

In accordance with some embodiments, the various delivery methods and systems can also be provided. For example, one or more devices can be delivered using the systems disclosed herein in combination with a catheter. The device delivery system can comprise an elongate tube or catheter which slidably receives a core assembly configured to carry the device through the catheter. The catheter can have a proximal end and an opposing distal end which can be positioned at a treatment site within a patient, an internal lumen extending from the proximal end to the distal end, and an inner surface or wall facing the lumen. At the distal end, the catheter has a distal opening through which the core assembly and/or the device may be advanced beyond the distal end in order to expand, release, or deploy the device within the target area, such as a blood vessel or aneurysm. The proximal end may include a catheter hub. The catheter can define a generally longitudinal axis A-A extending between the proximal end and the distal end. When the delivery system is in use, the longitudinal axis need not be straight along some or any of its length.

The catheter can optionally comprise a microcatheter. For example, the catheter can optionally comprise any of the various lengths of the MARKSMAN™ catheter available from Covidien LP of Irvine, Calif. USA. The catheter can optionally comprise a microcatheter having an inner diameter of about 0.030 inches or less, and/or an outer diameter of 3 Fr or less near the distal end. Instead of or in addition to these specifications, the catheter can comprise a microcatheter which is configured to percutaneously access the internal carotid artery, or a location within the neurovasculature distal of the internal carotid artery, with its distal opening.

Information regarding additional embodiments of the catheter, and additional details and components that can optionally be used or implemented in the embodiments of the catheter described herein, can be found in U.S. Patent Application Publication No. US 2011/0238041 A1, published on Sep. 29, 2011, titled Variable Flexibility Catheter. The entirety of the aforementioned publication is hereby incorporated by reference herein and made a part of this specification.

Figure 7A:
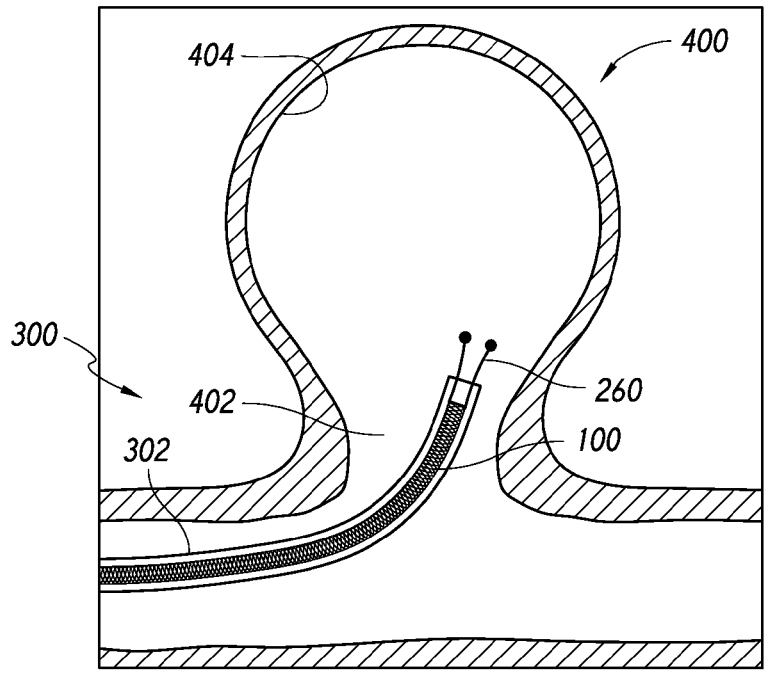
FIGS. 7A-7F illustrate progressive steps in the deployment of a device into an aneurysm, according to some embodiments.
Figure 7B:
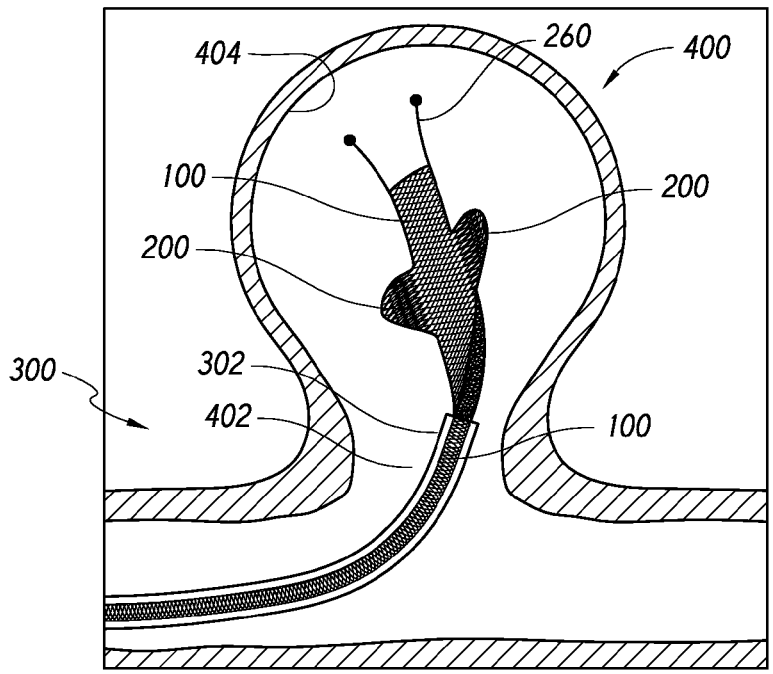

FIGS. 7A-7F illustrate aspects of a delivery assembly 300 and occlusive device 100 that has been advanced to a target aneurysm 400. As illustrated in FIGS. 7A-7B, the device 100 can be advanced through a neck 402 of the aneurysm 400 toward the fundus 404 of the aneurysm 400. As the device 100 is advanced into the aneurysm 400, the device 100 can tend to uncurl, unroll, or expand from its collapsed configuration such that the opposing edges of the device move apart from each other and the released portion of the device 100 begins to assume a generally flat cross-sectional configuration.

Figure 7C:
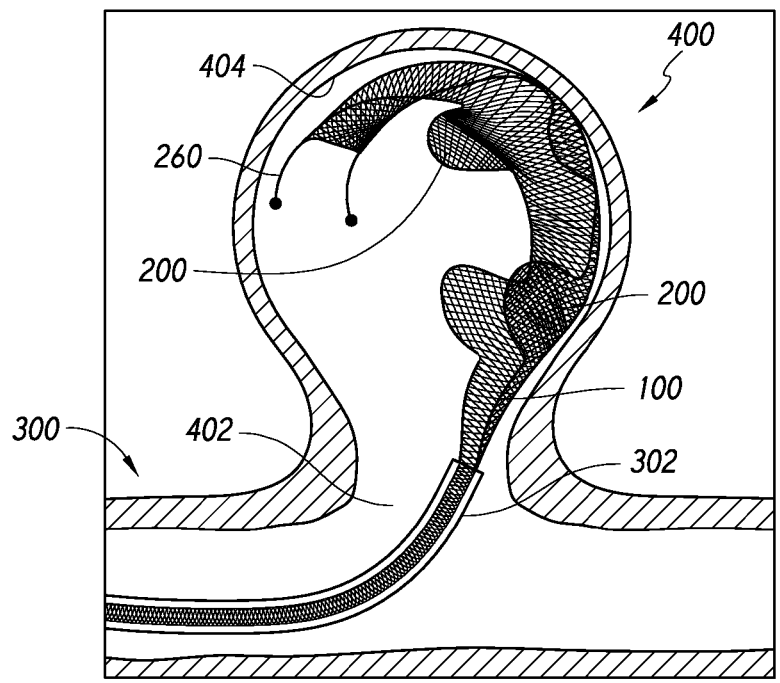
Figure 7D:
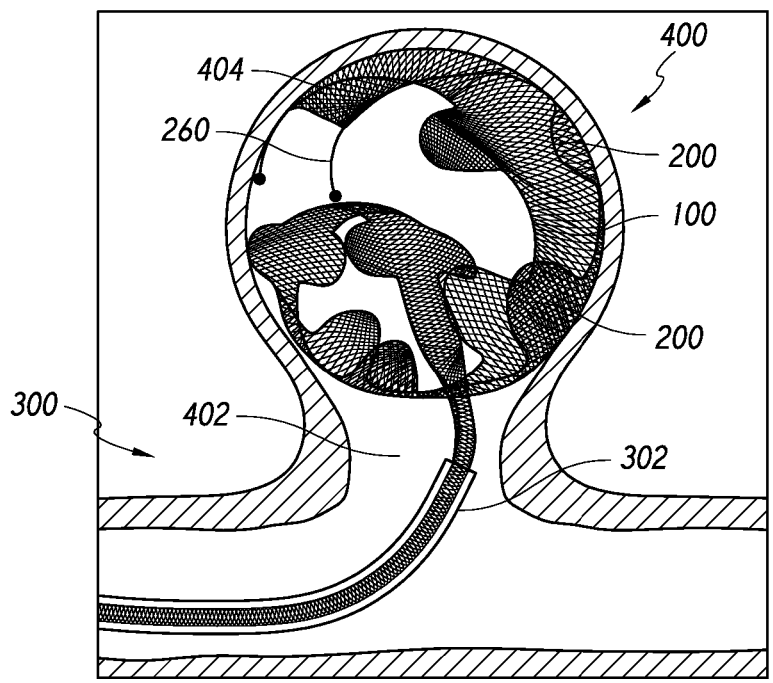

As the device 100 continues to be advanced into the aneurysm 400, as shown in FIGS. 7C-7D, the enlarged portions 200 of the device 100 and the body 150 of the device 100 can contact the inner wall or fundus 404 of the aneurysm 400. As the enlarged portions 200 and the body 150 contact the inner wall of the aneurysm 400, the device 100 can tend to frictionally contact or engage the inner wall of the aneurysm 400, thus reducing or eliminating slipping or sliding against the inner wall of the aneurysm 400, while maintaining the ability of the device 100 to conform and move freely within the aneurysm 400 during initial expansion and entry of the device 100 into the aneurysm 400. Accordingly, once a length of the device 100 is released into the aneurysm 400, which can be from about ¼ to about ¾, or from about ⅓ to about ⅔, or about ½ of the length of the device 100, the device 100 can tend to engage the inner wall of the aneurysm 400. Such engagement can allow the clinician to better predict the deployment characteristics or released position of the device 100 within the aneurysm 400. Additionally, such engagement can also enable the device 100 to be more securely retained within the aneurysm 400, thereby avoiding herniation of the device 100 from within the aneurysm 400.

Figure 7E:
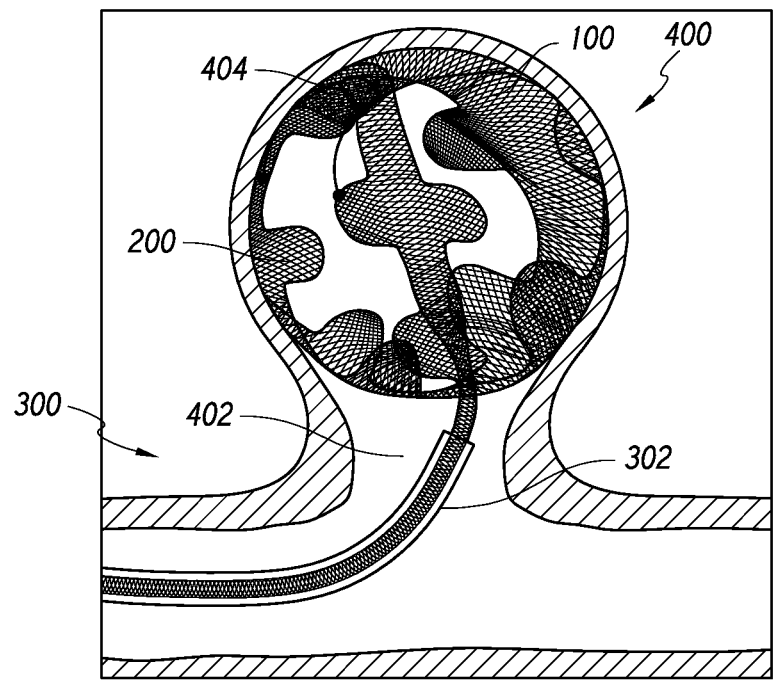
Figure 7F:
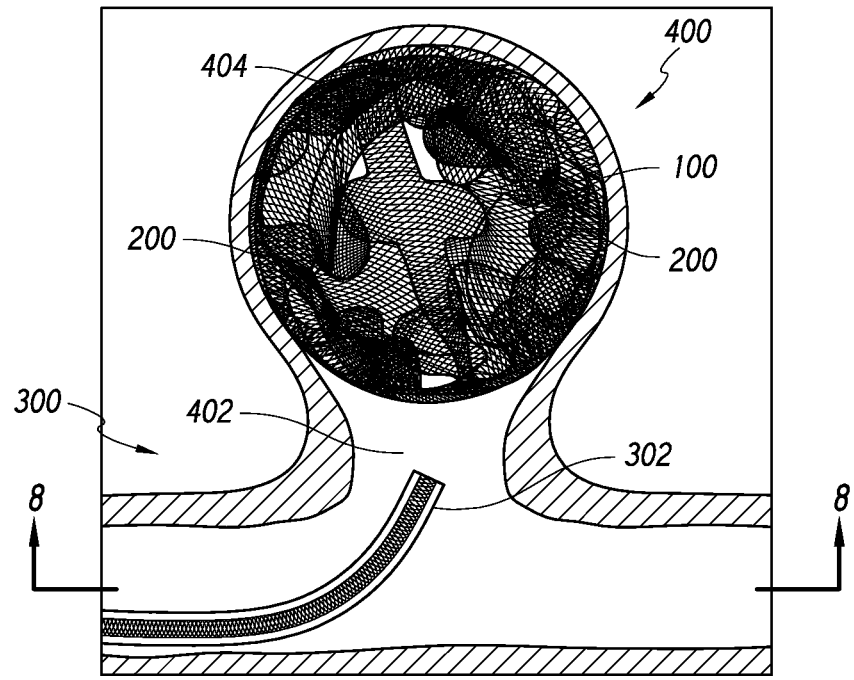
Figure 8:
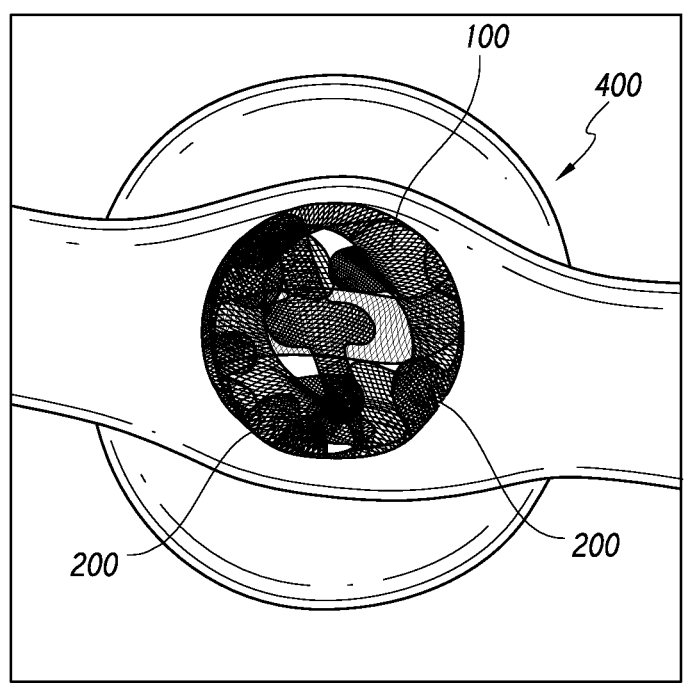
FIG. 8 illustrates coverage of a neck of an aneurysm using one or more devices, according to some embodiments.

Additionally, as illustrated in FIGS. 7E-7F, as the device 100 continues to advance into the aneurysm 400, the neck 402 will tend to be fully covered or blocked. For example, as the body 150 and additional enlarged portions 200 continue to be advanced into the aneurysm 400, the wings 200 and body 150 will tend to engage the inner wall of the aneurysm 400 extending over the neck 402. Eventually, whether a single or multiple devices are inserted into the aneurysm 400, the volume of the aneurysm 400 can be substantially packed or filled such that circulation or fluid movement is slowed or stopped within the aneurysm 400 and in to the aneurysm 400 through the neck 402 is substantially slowed or stopped. FIG. 8 illustrates a view into the aneurysm 400 from below the aneurysm neck 402 after the device 100 or multiple devices are released into the aneurysm 400. The use of devices having the enlarged portions 200, although optional, can further improve the coverage of the neck 402 and engagement with the sidewall of the aneurysm 400.

Referring again to FIG. 8, substantial coverage of the aneurysm neck 402 using a device that has a textured surface, such as those mentioned above, including the braided or coated surfaces, can beneficially facilitate and invoke a healing response. Thus, superior neck coverage can allow endothelialization to more easily take place at the neck 402. Accordingly, some embodiments can be provided in which a single device is used to treat a wide neck aneurysm, in contrast to traditional treatments that require both a coil and the placement of a stent or other framing structure to prevent herniation of the coil from within the wide neck aneurysm.

In accordance with some embodiments, the delivery of one or more occlusive devices can be performed by delivering only a single occlusive device or multiple occlusive devices. For example, a first device can be released into the aneurysm that can function as the outermost layer of the group of devices deployed into the aneurysm. Subsequent devices can thereafter be inserted within the first framing device within the aneurysm. Such additional devices can comprise finishing coils or additional devices, such as those disclosed herein. The size and/or shape of the coils or devices subsequently released into the aneurysm can be progressively smaller or of a substantially identical or different size and/or shape.

According to one of the advantageous features of some embodiments disclosed herein, one or more devices can be delivered into the aneurysm without requiring the use of a framing structure to hold the devices within the aneurysm, which is required when using coils. Further, much better than coils, the devices disclosed herein can provide excellent neck coverage. Furthermore, much better than coils, the devices disclosed herein can reliably and predictably expand to preset shapes or configurations. Moreover, in contrast to stents or expandable braided structures, such as braided balls, the devices disclosed herein can pack or fill the volume of the target space, such as an aneurysm, much as coils are able to do. These and other such advantages disclosed herein, which traditionally are only achieved through multiple, separate components, can therefore be achieved using embodiments of the devices disclosed herein.

When delivering multiple devices into the aneurysm, the length of the devices, and in some embodiments, coils, can be between about 1 cm to about 10 cm. The order of delivery of such devices can be in order of progressive decrease in size. For example, the clinician can start with an 8 mm device, followed by one or more 7 mm devices, followed by one or more 6 mm devices, and so forth.

As noted above, the device 100 can comprise a nitinol or other material that tends to have a highly predictable shape when in the relaxed or released position. Thus, in contrast to coils, that will not tend to achieve a highly predictable shape (thereby being more random in their relaxed state), embodiments of the device 100 can advantageously allow a clinician to provide a specifically shaped device to a target area of a specific shape or size. Such tailored therapy can improve the outcome for patients.

The apparatus and methods discussed herein are not limited to the deployment and use of a medical device within the vascular system but may include any number of further treatment applications. Other treatment sites may include areas or regions of the body including any hollow anatomical structures.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. An occlusive device for occluding an aneurysm, comprising:
    an elongate member formed of a single layer sheet of mesh material having a longitudinal axis, opposing first and second side edges extending longitudinally along the member, and a body extending laterally between the first and second side edges, wherein the member has: (a) a collapsed configuration for delivery through a catheter to the aneurysm, wherein, in the collapsed configuration, the member is rolled about a line parallel to the longitudinal axis of the member such that a first portion of the body is positioned radially inward of and overlaps a second portion of the body; and (b) an expanded configuration in which the member forms a substantially spherical three-dimensional shape.

2. The device of claim 1, wherein the first and second side edges comprise a plurality of wing elements extending laterally therefrom.

3. The device of claim 1, wherein the wing elements extend from opposing sides of the elongate member.

4. The device of claim 3, wherein a pair of wing elements extend from opposing sides at a first longitudinal position along the member.

5. The device of claim 3, wherein the wing elements comprise first and second sets of wing elements, the first set extending from a first side of the member and the second set extending from a second side of the member at different longitudinal positions than the first set.

6. The device of claim 1, wherein only the cross-sectional outer portion of the member contacts an inner wall of the catheter when the member is positioned within the catheter.

7. The device of claim 1, wherein the elongate member comprises a superelastic material.

8. The device of claim 1, wherein the mesh material comprises a plurality of interwoven filaments.

9. The device of claim 1, wherein the member is configured to self-expand from the collapsed configuration to the expanded configuration when the member is released from the catheter.

10. The device of claim 1, wherein the elongate member comprises at least one slit extending along the longitudinal axis of the member.

11. The device of claim 1, wherein the elongate member comprises a plurality of slits extending along the longitudinal axis of the member and spaced apart in a linear configuration.

12. The device of claim 1, wherein the member is folded.

13. The device of claim 12, wherein the member is folded two times.

14. The device of claim 12, wherein the member is folded three times.

15. The device of claim 1, further comprising an atraumatic portion extending distally from its distal end.

16. The device of claim 1, further comprising a radiopaque marker.

17. The device of claim 1, wherein the member is configured to be implanted within a cerebral aneurysm.

18. An occlusive device, comprising:
an elongate member formed of a continuous sheet of material, the member having a longitudinal axis, and a body extending (i) longitudinally along the member and (ii) laterally between edges of the member, wherein the member comprises—
a collapsed configuration for delivery through a catheter, wherein, in the collapsed configuration, the member is rolled about a line parallel to the longitudinal axis of the member; and
an expanded configuration in which the member forms a substantially spherical three-dimensional shape and is configured to be implanted within a cerebral aneurysm.

19. The device of claim 18, wherein the member includes a wing element having first and second edges that (i) converge toward one another and (ii) extend from one of the edges of the member.

20. The device of claim 18, wherein the member comprises a mesh material, a laser-cut sheet, or a photo-etched sheet.

* * * * *